US008660694B2

(12) United States Patent
Lurz et al.

(10) Patent No.: US 8,660,694 B2
(45) Date of Patent: Feb. 25, 2014

(54) METHOD FOR COMPUTER-AIDED MOVEMENT PLANNING OF A ROBOT

(76) Inventors: Winfried Lurz, Fürth (DE); Werner Neubauer, München (DE); Manfred Schönborn, Gerhardshofen (DE)

( * ) Notice: Subject to any disclaimer, the term of this patent is extended or adjusted under 35 U.S.C. 154(b) by 1090 days.

(21) Appl. No.: 12/431,258

(22) Filed: Apr. 28, 2009

(65) Prior Publication Data

US 2009/0271035 A1  Oct. 29, 2009

(30) Foreign Application Priority Data

Apr. 29, 2008 (DE) .......................... 10 2008 021 386
Nov. 13, 2008 (DE) .......................... 10 2008 057 142

(51) Int. Cl.
*G06F 19/00* (2011.01)

(52) U.S. Cl.
USPC ........................................... 700/255; 901/16

(58) Field of Classification Search
USPC ....................................... 700/251, 255; 901/16
See application file for complete search history.

(56) References Cited

U.S. PATENT DOCUMENTS

| | | | | |
|---|---|---|---|---|
| 4,987,583 A * | 1/1991 | Travanty et al. | ................ | 378/91 |
| 5,347,459 A * | 9/1994 | Greenspan et al. | ........... | 700/255 |
| 5,889,926 A * | 3/1999 | Bourne et al. | ................ | 700/255 |
| 6,493,607 B1 * | 12/2002 | Bourne et al. | ................ | 700/255 |
| 7,530,739 B2 | 5/2009 | Lurz et al. | | |
| 7,746,978 B2 * | 6/2010 | Cheng et al. | .................... | 378/65 |
| 7,801,644 B2 * | 9/2010 | Bruemmer et al. | ........... | 700/249 |
| 2001/0005410 A1 * | 6/2001 | Rasche et al. | ................ | 378/197 |
| 2005/0075563 A1 * | 4/2005 | Sukovic et al. | ................ | 600/427 |
| 2005/0281374 A1 * | 12/2005 | Cheng et al. | .................... | 378/68 |
| 2007/0156157 A1 * | 7/2007 | Nahum et al. | ................ | 606/130 |
| 2008/0013690 A1 | 1/2008 | Lurz et al. | | |
| 2009/0003975 A1 * | 1/2009 | Kuduvalli et al. | ............ | 414/146 |

FOREIGN PATENT DOCUMENTS

| | | |
|---|---|---|
| DE | 19625637 A1 | 1/1998 |
| DE | 19810341 A1 | 9/1999 |
| DE | 10200534 A1 | 7/2003 |
| DE | 102006007623 A1 | 8/2007 |
| DE | 102006028327 B3 | 1/2008 |
| EP | 1862876 A1 | 12/2007 |

OTHER PUBLICATIONS

Lydia E. Kavraki, Jean-Claude Latombe, "Probabilistic Roadmaps for Robot Path Planning", Department of Computer Scince, Rice University, Houston, TX 77005, Department of Computer Science, Stanford University, Stanford, CA 94305, 1997, pp. 1-21.

(Continued)

*Primary Examiner* — Jason Holloway

(57) ABSTRACT

A method for computer-aided movement planning of a robot is provided, in which a trajectory for the movement of a spatial point assigned to the robot is planned in a fixed coordinates system. The spatial positions are translated from a plurality of spatial positions of the spatial point into respective configuration positions in a configuration room of the robot based on inverse kinematics. The respective configuration positions are described by axial positions of one or several rotatory or translational movement axes of the robot and are tested for collisions and a trajectory is formed along spatial positions of the spatial point, the respective configuration positions of which are collision-free. Planning the movement in a fixed coordinates system improves the efficiency of the planning method and the planned movement corresponds more to the expectations of the persons or the operating staff in the surroundings of the robot.

13 Claims, 2 Drawing Sheets

(56) References Cited

OTHER PUBLICATIONS

Gildardo Sanchez and Jean-Claude Latombe, "A Single-Query Bi-Directional Probabilistic Roadmap Planner with Lazy Collision Checking", 2001 Int. Symp. Robotics Research, pp. 1-10.

C. Nissoux, T> Simeon and J-P. Laumond, "Visibility Based Probabilistic Roadmaps", IEEE Int. Conf. on Intelligent Robots and Systems, 1999, pp. 1-6.

* cited by examiner

METHOD FOR COMPUTER-AIDED MOVEMENT PLANNING OF A ROBOT

CROSS REFERENCE TO RELATED APPLICATIONS

This application claims priority of German application No. 10 2008 021 386.1 filed Apr. 29, 2008 and German application No. 10 2008 057 142.3 filed Nov. 13, 2008, both of the applications are incorporated by reference herein in their entirety.

FIELD OF THE INVENTION

The invention relates to a method and a device for computer-aided movement planning of a robot.

BACKGROUND OF THE INVENTION

The movement planning of robotic systems aims at ensuring a collision-free movement of the robotic system between a corresponding start and target position. A collision-free movement trajectory along a plurality of intermediate positions is determined in this way using suitable planning methods, said intermediate positions being linked to one another by way of trajection elements.

In known movement planning methods, the individual intermediate points and/or trajectory elements in the so-called configuration room are planned. The configuration room is described here by means of axial positions of one or several rotatory and/or translational movement axes of the robotic system. With known methods, a collision-free trajectory is thus calculated in the configuration room. Testing a configuration position for collision freedom proceeds such that based on the known forward kinematics of the robotic system, the geometry of the system is calculated in a stationary base coordinates system which does not move with the robot and a test is carried out for collisions with correspondingly stored objects in the base coordinates system.

In conventional planning methods, the trajectory elements between the collision-free positions in the configuration room are generally straight. This is problematic in that straight movements in the configuration room in the stationary base coordinates system are often significantly curved particularly in the case of the articulated arm kinematics of the robotic system. With curved movements, collisions are significantly more likely than with a straight movement in the stationary base coordinates system. The planning effort and planning times involved in conventional planning methods are thus very high since a plurality of configuration positions have to be tested until a collision-free trajectory is found. Furthermore, a curved movement in the stationary base coordinates system is not very plausible for persons and/or operating personnel in the surroundings of the robotic system and is thus rarely accepted.

SUMMARY OF THE INVENTION

The object underlying the invention is to create a method and a device for movement planning of a robot, which shortens the computing time needed for a collision-free movement trajectory of a robot.

This object is achieved by a method or a device according to the independent claims. Further advantageous embodiments of the invention are defined in the dependent claims.

In the method according to the invention, a trajectory for the movement of a spatial point assigned to the robot is planned in a stationary coordinates system, with the stationary coordinates system illustrating the already afore-cited base coordinates system. This coordinates system is frequently also referred to as a world coordinates system. In order to calculate a trajectory of this type, spatial positions from a plurality of spatial positions of the spatial point are translated into the respective configuration positions in the configuration room of the robot based on inverse kinematics. As already mentioned above, a respective configuration position is described by means of an axial position and/or axial positions of one or several rotatory and/or translational movement axes of the robot.

Translations based on inverse kinematics are known sufficiently from the robotics. The inverse kinematics allow a spatial position of a spatial point assigned to the robot in the world coordinates system to be translated into corresponding configuration positions in the configuration room. In contrast to inverse kinematics, a corresponding position of the robot in the base coordinates system is calculated from a configuration position in the configuration room using the already afore-mentioned forward kinematics.

In accordance with the invention, the respectively translated configuration positions are tested for collisions and a trajectory is formed along spatial positions of the spatial point based hereupon, the respective configuration positions of which are collision free. A test is carried out in turn for collision freedom using the method known per se. In particular, the geometry of the robot is calculated in the base coordinates system using the forward kinematics and this then determines whether collisions occur with stored objects in the base coordinates system.

The method according to the invention relates to the knowledge that the planning of a trajectory in the stationary base coordinates system can take place over minimal computing time, since partial trajectory elements in the base coordinates system are now more than likely to be collision-free. Furthermore, trajectories can be planned which correspond to the expectations of a user in respect of a collision-free path between two points.

In a particularly preferred embodiment of the method according to the invention, the spatial point assigned to the robot is the tool center point thereof. The tool center point is a term known sufficiently from robotics and relates to the end effector of a robot, i.e. the last element of the kinematics chain of a robot.

In a further preferred embodiment, the stationary coordinates system is a Cartesian coordinates system with orthogonal axes and/or the movement of the robot is planned in the three-dimensional space.

In a particularly preferred embodiment, the planned trajectory is formed by straight trajectory elements between the spatial positions of the spatial point. As a result, a particularly computing-efficient calculation of the trajectory is achieved in the stationary coordinates system.

In a further embodiment of the method according to the invention, in the event that no configuration position can be determined in the configuration room at a spatial position of the spatial point based on the inverse kinematics, this spatial position is not taken into consideration during the movement planning. In this way, a suitable treatment of spatial positions, which cannot be achieved as a result of the kinematics of the robot, takes place.

In a further embodiment of the method according to the invention, if, based on the inverse kinematics for a spatial position of the spatial point, an ambiguous configuration including several configuration positions which are possible for the spatial position is found, one of the configuration positions is selected from the ambiguous configuration according to predetermined criteria and is used for collision checks. The predetermined criteria can be embodied differently, if necessary one of the configuration positions can be selected randomly.

In a particularly preferred variant of the invention, in the case of an ambiguous configuration occurring, that configuration is selected from the ambiguous configuration position, the distance of which from the configuration position of the spatial point previously lying on the trajectory being at its lowest. An erratic change between different configuration positions is avoided in this way.

In a further configuration of the method according to the invention, the movement planning is carried out using a probabilistic planning method or using a control-based planning method or using a planning method based on the potential field method. With probabilistic planning methods, random spatial positions are selected one after the other and the trajectory is formed as a result. With control-based planning methods, different sets of rules are specified, on the basis of which a change in the robot position is to take place. With the potential field method, a repellent potential field is modeled about objects in the stationary base coordinates system in order to prevent collisions with these objects as a result.

The method according to the invention can be used for any robotic systems. A preferred application is the planning of the movement of a robotic medical device, in particular an imaging medical device. The medical device is preferably a robot-controlled C-arm, with which patients are x-rayed. X-ray devices in the form of C-arms are known sufficiently from the prior art. The movement is preferably planned here in respect of the isocenter of the C-arm. The isocenter here represents the tool center point of the C-arm.

In addition to the afore-described method, the invention also relates to a device for the computer-aided movement planning of a robot, with a trajectory for the movement of a spatial point assigned to the robot being planned during operation of the device in a stationary coordinates system. To this end, the device includes a means for translating spatial positions from a plurality of spatial positions of the spatial point into respective configuration positions in a configuration room of the robot based on inverse kinematics, with a respective configuration position being described by axial positions of one or several rotatory and/or translational movement axes of the robot. Furthermore, the device contains a means for testing the respective configuration positions for collisions and a means for forming a trajectory along spatial positions of the spatial point, the respective configuration positions of which are collision-free.

The device is preferably embodied here such that each variant of the afore-described planning method can be implemented with the device.

The invention also includes a robot, in particular a robotic medical device, which contains the afore-described device according to the invention.

BRIEF DESCRIPTION OF THE DRAWINGS

Exemplary embodiments of the invention are described in more detail below with reference to the appended figures.

The FIG. 1 is a schematic representation of a robot controlled x ray device, the movement of which is planned based on an embodiment of the method according to the invention.

DETAILED DESCRIPTION OF THE INVENTION

Figure 1:
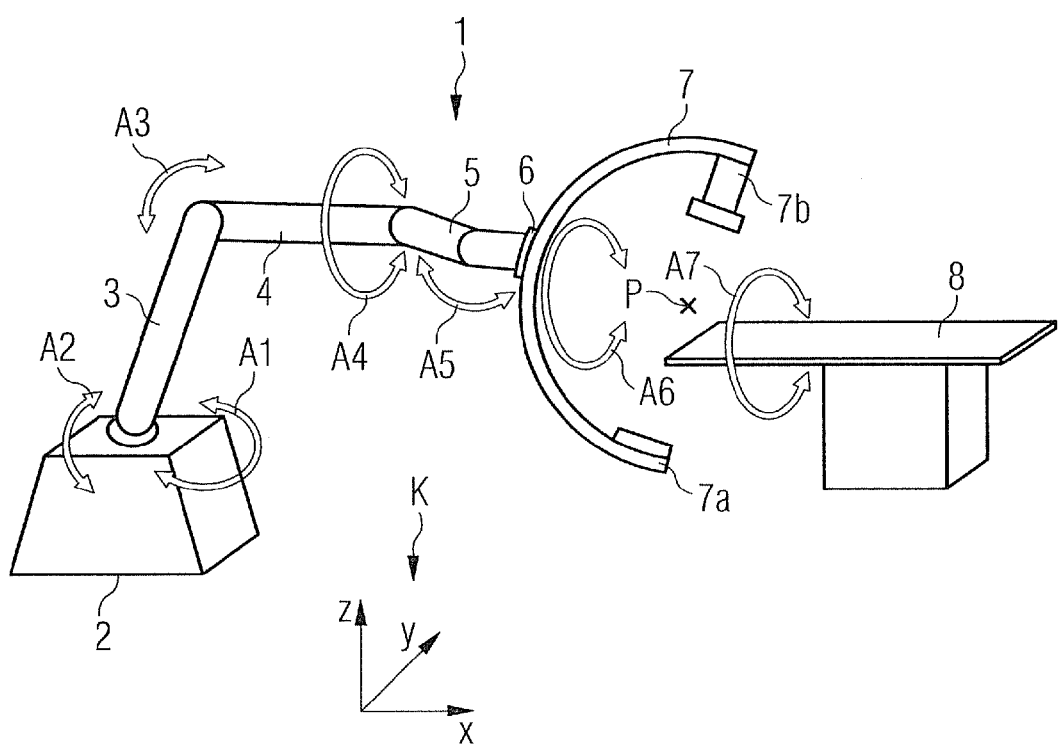
Figure 2:
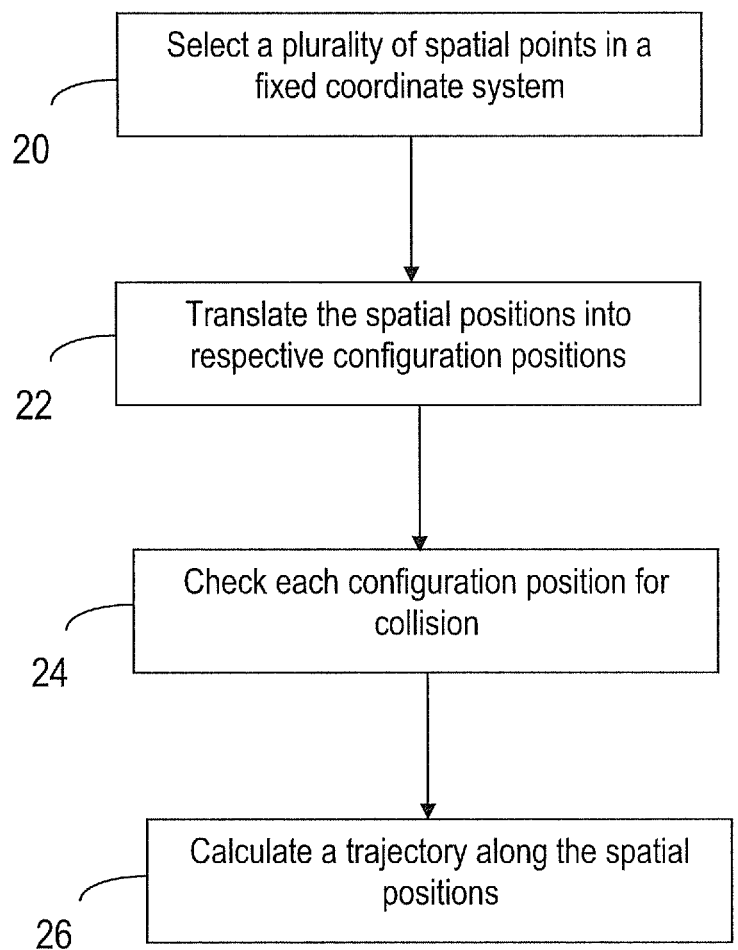
FIG. 2 shows a logic flow diagram of the method steps.

The robot-controlled x-ray device 1 shown in FIG. 1 includes a base frame 2, which can be fixedly mounted to the base of an operating theater for instance. A carousel (not shown in detail) is positioned on the base frame, said carousel enabling a movement of a system comprising arms and joints about a vertically moving axis A1. The system comprising arms and joints includes a rocker arm 3, which can be pivoted about a second axis of rotation A2. An arm 4 is fastened to the rocker arm 3 in a rotatable fashion about a third axis of rotation A3. A robotic hand 5 is attached to the end of the arm 4 so as to be rotatable about a fourth axis of rotation A4, said robotic hand having an interface 6 for coupling a so-called C-arm 7. The C-arm can be rotated here via the interface 6 about an axis of rotation A6 and can be pivoted about a fifth axis of rotation A5 which runs at right angles thereto.

The C-arm 7 includes an x-ray detector 7a on its front ends as well as a corresponding x-ray source 7b. The center point between the x-ray detector 7a and x-ray source 7b represents the isocenter P of the C-arm and forms the end effector and/or tool center point of the robot 1. For x-ray purposes, the tool center point P of the robot 1 on an organ of a patient to be x-rayed on the patient couch 8 is moved and several two-dimensional x-ray recordings are then identified with the aid of the x-ray detector 7a and the x-ray source 7b. Here the x-ray recordings are generated in different positions of the C-arm about the axis A7 running along the patient couch 8.

To now prevent collisions of the robot 1 with any objects in the room, the movement of the robot to be implemented is planned in advance. In this way a plurality of positions of the robot is consequently monitored in the space to determine whether collisions occur in the individual positions. Collision-free positions are then combined to form a trajectory, along which the robot can then move between a predetermined start and target position.

In conventional methods for movement planning, the planning of the movement takes place in the so-called configuration room, which is described by the individual axial angles of the axes A1 to A6 according to FIG. 1. If necessary, the configuration room may in addition to rotatory axial positions also feature translational axial positions. By way of example, the C-arm can also be moved up and down on the interface 6 in a translational fashion in the plane spanned by the C-arm. When planning the movement of the C-arm in the configuration room, collision calculations are implemented for a plurality of positions in this configuration room until a trajectory is found in the configuration room which connects a predetermined start and target position without collisions to one another. The geometry of the robot and the position of the tool center point P is calculated here for each position in the configuration room from the axial position values of the robot with the aid of the forward kinematics, which can be described by means of a matrix multiplication. The robot geometry and the position of the tool center point is specified in respect of a stationary Cartesian world coordinates system which does not move with the robot, with such a coordinates system for instance being identified in FIG. 1 with K and including the axes x, y and z.

In accordance with the invention, the planning of the movement of the robot is from now on not carried out in the configuration room of the axial positions A1 to A6, but instead in the world coordinates system K. Here the movement of the tool center points P is planned directly. In particular, corresponding collision calculations are implemented for a plurality of positions of the tool center point P in the world coordinates system K. To this end, the corresponding axial positions A1 to A6 are calculated in the configuration room with the aid of the inverse kinematics of the robot from each position of the tool center point P in order to implement a collision calculation herefor. Specifically, as shown in FIG.

2, a plurality of spatial points in a fixed coordinate system are selected in step 20. In step 22 the plurality of spatial positions are translated into respective configuration positions. In step 24 each configuration position is checked for a collision, and in step 26 a trajectory is calculated along the spatial positions.

If necessary, ambiguities may occur with the translation of the position of the tool center point to the axial positions of the configuration room, since several arm positions are possibly feasible for the same position of the tool center point as a result of the articulated arm kinematics of the robot 1. A configuration is then selected according to certain criteria. In the simplest case, the configuration can be selected randomly. It should however be ensured that when changing the tool center point from one position to the next, the corresponding configurations in the configuration room are not changed erratically.

Furthermore, it may occur during the planning of the movement in the coordinates system K that a position of the tool center point P in the configuration room cannot be achieved. In this case, the corresponding position of the tool center point is treated as a position which leads to collisions so that this position is no longer considered during the movement planning.

The movement planning of the tool center point P in the stationary coordinates system K is advantageous in that the trajectory is planned in a room which is visible for the user, so that the calculated trajectory of the movement planning is plausible for the user and also corresponds to the expectations of the user. Furthermore, the individual partial trajectories of the planned movement trajectory are more likely to be collision-free than if the trajectory is planned in the configuration room.

The invention claimed is:

1. A method for planning a movement of a robot in a fixed coordinate system of a spatial point assigned to the robot, comprising:
    calculating a geometry of the robot from a plurality of predetermined spatial positions of the spatial point based on a forward kinematics using a computing processor;
    translating the plurality of predetermined spatial positions of the spatial point into respective configuration positions in a configuration room of the robot using a translating processor based on an inverse kinematics, wherein each respective configuration position is described by at least one rotary and/or translational movement axis of the robot;
    checking the geometry of the robot with the respective configuration positions for a collision using a testing processor; and
    calculating a trajectory along the predetermined spatial positions based on a result of the checking using the computing processor so that the respective configuration positions of the trajectory are collision-free.

2. The method as claimed in claim 1, wherein the spatial point is a tool center point of the robot.

3. The method as claimed in claim 2, wherein the fixed coordinates system is a Cartesian coordinates system.

4. The method as claimed in claim 3, wherein the movement is a three-dimensional movement.

5. The method as claimed in claim 1, wherein the trajectory is formed by a straight trajectory elements between different spatial positions of the spatial point.

6. The method as claimed in claim 1, wherein upon said translating a given spatial position of the spatial point into a plurality of configuration positions, said method further comprises selecting one of the plurality of respective configuration positions according to a predetermined criteria.

7. The method as claimed in claim 6, wherein the selected respective configuration position is selected because it has a lowest distance from a respective configuration position of a spatial point previously lying on the trajectory.

8. The method as claimed in claim 1, wherein the method comprises selecting the plurality of spatial positions using a probabilistic planning method, a control-based planning method, and/or a potential field planning method.

9. The method as claimed in claim 1, wherein the robot moves a robotic medical device.

10. The method as claimed in claim 9, wherein the robotic medical device is a robot-controlled C-arm and the spatial point is an isocenter of the C-arm.

11. The method as claimed in claim 1, wherein the movement is computer-aided.

12. A device for planning a movement of a robot in a fixed coordinate system of a spatial point assigned to the robot, comprising:
    a computing processor that calculates a geometry of the robot from a plurality of predetermined spatial positions of the spatial point based on a forward kinematics using a computing processor;
    a translating processor that translates a plurality of predetermined spatial positions of the spatial point into respective configuration positions in a configuration room of the robot based on an inverse kinematics, each respective configuration position being described by a movement axis of the robot; and
    a testing processor that tests the geometry of the robot with the respective configuration positions for a collision,
    wherein the computing processor calculates a trajectory along the predetermined spatial positions of the spatial point based on a result of the test so that the respective configuration positions of the trajectory are collision-free.

13. A robotic medical device, comprising:
    a robot comprising a spatial point, wherein the spatial point moves in a trajectory; and
    a processor configured to determine the trajectory that:
        calculates a geometry of the robot from a plurality of predetermined spatial positions of the spatial point based on a forward kinematics using a computing processor,
        translates a plurality of predetermined spatial positions of the spatial point into respective configuration positions in a configuration room of the robot based on inverse kinematics, each respective configuration position being described by a movement axis of the robot,
        tests the geometry of the robot with the respective configuration positions for a collision, and
        calculates the trajectory along the predetermined spatial positions of the spatial point based on a result of the test so that the respective configuration positions of the trajectory are collision-free.

* * * * *